US006933110B1

(12) United States Patent
Paranhos-Baccala et al.

(10) Patent No.: US 6,933,110 B1
(45) Date of Patent: Aug. 23, 2005

(54) TRYPANOSOMA CRUZI ANTIGEN, GENE ENCODING THEREFOR AND METHODS OF DETECTING AND TREATING CHAGAS DISEASE

(75) Inventors: Glaucia Paranhos-Baccala, Lyons (FR); Mylene Lesenechal, Villeurbanne (FR); Michel Jolivet, Bron (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/138,735

(22) Filed: Aug. 24, 1998

Related U.S. Application Data

(62) Division of application No. 08/480,917, filed on Jun. 7, 1995, now Pat. No. 5,820,864.

(30) Foreign Application Priority Data

Aug. 12, 1994 (FR) ............................................. 94 10132

(51) Int. Cl.$^7$ ........................... C12Q 1/68; C07H 21/02; C07H 21/04
(52) U.S. Cl. ........................ 435/6; 536/23.1; 536/23.7; 536/24.3; 536/24.32; 536/24.33
(58) Field of Search .................. 435/6, 320.1; 536/23.1, 536/23.7, 24.3, 24.32, 24.33, 24.1, 24.2; 424/269.1

(56) References Cited

U.S. PATENT DOCUMENTS

| 5,256,545 A | * 10/1993 | Brown et al. ............... 435/69.1 |
| 5,302,527 A | * 4/1994 | Birkett et al. |
| 5,312,746 A | * 5/1994 | Longo et al. ............... 435/193 |
| 5,474,925 A | * 12/1995 | Barton et al. |
| 5,495,070 A | * 2/1996 | John |
| 5,550,027 A | 8/1996 | Winkler et al. |

FOREIGN PATENT DOCUMENTS

| FR | A-2452288 | 10/1980 |
| WO | WO-A-9117759 | 11/1991 |
| WO | WO-A-9401776 | 1/1994 |

OTHER PUBLICATIONS

Gencore Accession #M30933. Ko et al, 1990.*
Gencore Accession #L27277. (from Opperman et al. J. Bacteriol. 1994. 176(16):5033–5043.*
Gencore Accession #JH0465. Porteus et al., 1991.*
Gencore Accession #P07746. Pentecost, 1985.*
E. De Gaspari et al., "*Trypanosoma cruzi*: Studies on the Reactivity of Antibodies Bound to the Surface of Blood Forms at the Early Phase of Infection," *Acta Tropica*, vol. 56, No. 1, Feb. 1994, pp. 79–87.
A. Gruppi et al., "*Trypanosoma cruzi* Exoantigens: Can Those Recognized By Sera from Chagasic Patients Trigger a Protective Immune Response in Mice?", *Res. Immunol.*, vol. 142, No. 9, 1991, pp. 821–828.

A. Katzin et al., "Rapid Determination of *Trypanosoma–cruiz* Urinary Antigens in Human Chronic Chagas Disease by Agglutination Test," *Experimental Parasitology*, vol. 68, No. 2, 1989, pp. 208–215.
N. Andrews et al., "Mapping of Surface Glycoproteins of *Trypanosoma cruzi* By Two–Dimensional Electrophoresis," *European Journal of Biochemistry*, vol. 140, No. 3, pp. 599–604.
G. Paranhos–Baccala et al., "Detection of Antibodies in Sera from Chagas Disease Patients Using a *Trypanosoma cruzi* Immunodominant Recombinant Antigen," *Parasite Immunology*, vol. 16, No. 3, Mar. 1994, pp. 165–169.
J. LaFaille et al., "Structure and Expression of Two *Trypanosoma cruzi* Genes Encoding Antigenic Proteins Bearing Repetitive Epitopes," *Molecular and Biochemical Parasitology*, vol. 35, 1989, pp. 127–136.
R. Young et al., "Efficient Isolation of Genes by Using Antibody Probes," *Proc. Natl. Acad. Sci.*, USA, vol. 80, Mar. 1983, pp. 1194–1198.
P. Cotrim et al., "Expression in *Escherichia coli* of a Dominant Immunogen of *Trypanosoma cruzi* Recognized by Human Chagasic Sera," *Journal of Clinical Microbiology*, vol. 28, No. 3, Mar. 1990, pp. 519–524.
F. Sanger, "DNA Sequencing with Chain–Terminating Inhibitors," *Proc. Natl. Acad. Sci.*, USA, vol. 74, No. 12, pp. 5463–5467, Dec. 1977.
U. Laemmli, "Cleavage of Structural Proteins During the Assembly of the Head of Bacteriophage T4," *Nature*, vol. 227, Aug. 15, 1970, pp. 680–685.
H. Towbin et al., "Electrophoretic Transfer of Proteins from Polyacrylamide Gels to Nitrocellulose Sheets: Procedure and Some Applications," *Proc. Natl. Acad. Sci.*, USA, vol. 76, No. 9, pp. 4350–4354, Sep. 1979.
D. Smith et al., "Single–step Purfication of Polypeptides Expressed in *Escherichia coli* as Fusions with Glutathione S–transferase," *Gene*, vol. 67, pp. 31–40, 1988.
A. Voller et al., "Microplate Enzyme–Linked Immunosorbent Assay for Chagas' Disease," *The Lancet*, Feb. 22, 1975, pp. 426–428.
M. Parsons et al., "*Trypanosoma* mRNAs Share a Common 5' Spliced Leader Sequence," *Cell*, vol. 38, pp. 309–316, 1984.
M. A. Frohman et al., "Rapid Production of Full–Length cDNAs from Rare Transcripts: Amplification Using a Single Gene–Specific Oligonucleotide Primer," *Proc. Natl. Acad. Sci.*, USA, vol. 85, pp. 8998–9002, Dec. 1988.
P. E. Nielsen et al., "Sequence–Selective Recognition of DNA by Strand Displacement with a Thymine–Substituted Polyamide," *Science*, vol. 254, Dec. 1991, pp. 1497–1500.

(Continued)

*Primary Examiner*—Mark Navarro
(74) *Attorney, Agent, or Firm*—Oliff & Berridge, PLC

(57) ABSTRACT

The nucleotide sequence of Tc100, a gene encoding PTc100, a new Trypanosoma antigen, and the amino acid sequence of PTc100 are described. Tc100 and PTc100, or fragments thereof, modified or otherwise, can be used directly or indirectly for the detection of *Trypanosoma cruzi*, or for the monitoring of the infection generated by *Trypanosoma cruzi*, in man or in animals.

16 Claims, 2 Drawing Sheets

OTHER PUBLICATIONS

T. Huynh et al., "Constructing and Screening cDNA Libraries in λgt10 and λgt 11," *Cloning: A Practical Approach*, pp. 49–78, D. Glover, ed. (1984).

N. Yoshida, "Surface Antigens of Metacyclic Trypomastigotes of *Trypanosoma cruzi*," *Infection and Immunity*, vol. 40, No. 2, May 1983, pp. 836–839.

A. Dunn et al., "A Novel Method to Map Transcripts: Evidence for Homology Between an Adenovirus mRNA and Discrete Multiple Regions of the Viral Genome," *Cell*, vol. 12, Sep. 1997, pp. 23–36.

E. Southern, "Detection of Specific Sequences Among DNA Fragments Separated by Gel Electrophoresis," *J. Mol. Biol.*, vol. 98, 1975, pp. 503–517.

*EMBL Gene Bank*, Hidelberg Brd., May 4, 1995, Accession No. U24190.

Kirchhoff et al., *J. Infect. Dis.*, Mar. 1987, vol. 155, No. 3, pp. 561–564.

* cited by examiner

SEQUENCE LISTING

<160> NUMBER OF SEQ ID NOS: 13

<210> SEQ ID NO 1
<211> LENGTH: 3402
<212> TYPE: DNA
<213> ORGANISM: Trypanosoma cruzi

<400> SEQUENCE: 1

```
aacgctatta ttagaacagt ttctgtacta tattgtcatt tggggagggg ggaaagggg      60 gaagtacttg ccgttttgtg tgggtgacga gacaacacac atcgagcggg aagaaaaaaa    120
aaaaggaaat aaattaaatt aaattatttg ttctttgaat aggcaaagaa gaagaagaag    180
aaaaggtgcg ggggagggag gagaaagcga cacacacaca aaaaaaaaaa aaggaattgc    240
ggaaataaca acgcaaggcg cggacatgac cgtgacggtg gatttgttca atcatgcgaa    300
gccgagcaac aatgagggcc gcgtgtggtc tgtggacgcc gcgacattta acgaggtgcc    360
tgaggcgcag cgtgtgctgg cggattcgca gttttatctt gcctacacca tgaagcggcg    420
tcacgtgctg cgtgtggtga agcgctcgaa cctttttgaag ggcaccgtgc gggcacactc    480
aaagcccatt catgcggtga agtttgtgaa ttaccgcagt aacgtcgcag catcggctgg    540 gaaggggag ttcttcgtgt gggttgtgac ggatgaaacg gaggcgagca acggcaagcc    600
ggatctcgca gcccgcctca cagtgaaggt gtactttaag cttcaggatc ctgtcacaat    660
tccatgcttt tctttcttta tcaacgccga gagtcagcgg cctgatctgc ttgtccttta    720
cgaaacgcag gcggcaattc ttgacagctc ctccctcatt gagcgctttg acgtggaatc    780
actggaggca acactacagc ggaattgcac aaccctgcga accctgactc aaccggttag    840
tgagaacagt ttatgctccg ttggctctgg cggatggttc acctttacca cggaaccaac    900
aatggtagcg gcatgcacat tacgaaaccg cagcactcca tcatgggcgt gttgcgaggg    960
tgagccagtg aaggcattgc atctccttga cgcaaccgtt gaggaaaatg tcagtgttct   1020
cgtggccgca tctacaaaag gggtgtacca atggctcctt acgggtgtag cagaaccaaa   1080
cttgttgcgc aagtttgtca ttgatggatc tattgtcgcg atggaaagct cacgagaaac   1140
gtttgccgtg tttgacgaca ggaagcagct ggcgctggtc aacatgcatt cccctcataa   1200
ctttacctgc acacactaca tgatgccttg tcaggtacag cgtaacggct tttgcttcaa   1260
```

```
tcgtacagcc gacggtagct gcgtcctggc tgacatgtcg attcgattga cgatcttcca    1320
tctccggtcc tcccgcaggg aagaacagca gccaggccaa aaacatcgg tagtggcgac     1380 ggcgaaaccg gggtgtgtgt cctcgggcac tgacgcggcg agtagcagtc ataccaatac    1440
gacttctgcc gctgctgcat ccctgcatc acccctgtt tcagcgccag ccaaggcagc      1500
cgcgcctcct gccgcggcgc gatcggctga gccgcacgtg gggagcaaga tcattgctaa    1560
tctagtgaat cagctgggga ttaatgtcac ccaaggagc gtcgtcagca ctggagcgcc     1620
ggccacgacg aggtctacgg cggtgacgtc acgactacc gccccgcagc gaacaagtcc     1680
atacgggcac aatggccgac ctgtgacggc tggattggtg gcagctaata gtggtgccag    1740
cgcggcctcg tctcccacag ccgcggcgaa accaacagga gaagaaaagg cctccgcggc    1800
atgtgaaacg agctccgtgg cgataaatgc gacacgcccg gcgcttcaca acgcctctct    1860
cccgcaggcg ccaacggatg gcgttttggc ggcagcagta taccagtcgg agggcgaggt    1920
tcatcagtcg ctggagcggc tggagtccgt cataaccaac acgtctcggg ttctgaagtt    1980
gctccctgac accattcgaa gagaccatga caacttctg aatctgggtt tagaggcaca     2040
gatgacagag ctgcagcaga gccgtccaac accgcaaaca cagccgagag acacaagctc    2100
cgcgaaatca tccgtgtttg agacgtacac ccttgttctc attgcggatt ccctctctcg    2160
caacatcacg aaggggtga agcgtggtgt gaacgaggcc attatgttgc atctcgacca    2220
tgaggtgcgg cacgccatag gaaccggct tcggcaaaca caaagaaca tcatcaagag      2280 ccgcctcgat gaagcgttga aggaaagcac tacacagttt acggctcaat tgacgcaaac    2340
ggtggagaat ctggtgaagc gcgagcttgc cgaggtgctt ggtagcatca acggctccct    2400
cacttctctc gtgaaggaaa atgcctcatt acagaaagag ttgaattcca taatgtctag    2460
tggggtgttg gatgaaatgc gtcgtatgcg ggaagagctg tgcacattgc gagagtccgt    2520
tgcgaagcgg aaggcaacaa tgccagattc ttctcttcac gccacgagct cctttcaagg    2580
aagaaggtct gcgcccgaga caattcttgc aaccgcgtta tcgatggtgc gagagcagca    2640
ataccgtcag ggactggaat acatgttgat ggctcagcag ccctctctcc tcctgcggtt    2700
cctcagcata cttacaaggg aaaacgaaaa cgcctactcg gaacttattg aaaatgtaga    2760
gacgccgaat gacgtgtggt gttcggttct gttgcaactc atagaggccg cggcgaccga    2820
ggctgagaag gaggtggttg ttggcgtcgc cattgatatt ctctccgagc gcgatcaaat    2880
tgctcagaac ggcgcactcg gctcgaaact caccaccgcc atgcgagcct ttgagcgaca    2940
ggcaaggtcg gagacaacga gcaggtcatt cttgcaatgc ctgaagaacc tggaaaagct    3000
tctgcaatca tgataataaa aagaactcaa cgaatacagt tgttgattat taaggaaggg    3060
aaaagagaga aagagagaga gagagagaga atgtaatgg gcgtttagtt acggtagaaa     3120
gaaaacgtgt ggataagaag gaggggtttt gtgtgcgacc aggaattact ggggaacgct    3180
gctacacggc ggaatcgacc attttattat tattattatt gtctttagta ttatgttttt    3240
tcttgtgtgt gtgtgtgtgt gtttgtgtgt gtgcggttat tttgtatccg tttgctcccg    3300 ccctgcccc ccatcacccg aggagaaagt agaataagac acatacgatt gttgtttttg     3360
ttatccttaa aaggaagaga gaccaaaaaa aaaaaaaaaa aa                       3402
```

<210> SEQ ID NO 2
<211> LENGTH: 915
<212> TYPE: PRT
<213> ORGANISM: Trypanosoma cruzi -continued

```
<400> SEQUENCE: 2

Met Thr Val Thr Val Asp Leu Phe Asn His Ala Lys Pro Ser Asn Asn
1               5                   10                  15

Glu Gly Arg Val Trp Ser Val Asp Ala Ala Thr Phe Asn Glu Val Pro
            20                  25                  30

Glu Ala Gln Arg Val Leu Ala Asp Ser Gln Phe Tyr Leu Ala Tyr Thr
        35                  40                  45

Met Lys Arg Arg His Val Leu Arg Val Val Lys Arg Ser Asn Leu Leu
    50                  55                  60

Lys Gly Thr Val Arg Ala His Ser Lys Pro Ile His Ala Val Lys Phe
65                  70                  75                  80

Val Asn Tyr Arg Ser Asn Val Ala Ala Ser Ala Gly Lys Gly Glu Phe
                85                  90                  95

Phe Val Trp Val Val Thr Asp Glu Thr Asp Ala Ser Asn Gly Lys Pro
            100                 105                 110

Asp Leu Ala Ala Arg Leu Thr Val Lys Val Tyr Phe Lys Leu Gln Asp
        115                 120                 125

Pro Val Thr Ile Pro Cys Phe Ser Phe Phe Ile Asn Ala Glu Ser Gln
    130                 135                 140

Arg Pro Asp Leu Leu Val Leu Tyr Glu Thr Gln Ala Ala Ile Leu Asp
145                 150                 155                 160

Ser Ser Ser Leu Ile Glu Arg Phe Asp Val Glu Ser Leu Glu Ala Thr
                165                 170                 175

Leu Gln Arg Asn Cys Thr Thr Leu Arg Thr Leu Thr Gln Pro Val Ser
            180                 185                 190

Glu Asn Ser Leu Cys Ser Val Gly Ser Gly Gly Trp Phe Thr Phe Thr
        195                 200                 205

Thr Glu Pro Thr Met Val Ala Ala Cys Thr Leu Arg Asn Arg Ser Thr
    210                 215                 220

Pro Ser Trp Ala Cys Cys Glu Gly Glu Pro Val Lys Ala Leu His Leu
225                 230                 235                 240

Leu Asp Ala Thr Val Glu Glu Asn Val Ser Val Leu Val Ala Ala Ser
                245                 250                 255

Thr Lys Gly Val Tyr Gln Trp Leu Leu Thr Gly Val Ala Glu Pro Asn
            260                 265                 270

Leu Leu Arg Lys Phe Val Ile Asp Gly Ser Ile Val Ala Met Glu Ser
        275                 280                 285

Ser Arg Glu Thr Phe Ala Val Phe Asp Asp Arg Lys Gln Leu Ala Leu
    290                 295                 300

Val Asn Met His Ser Pro His Asn Phe Thr Cys Thr His Tyr Met Met
305                 310                 315                 320

Pro Cys Gln Val Gln Arg Asn Gly Phe Cys Phe Asn Arg Thr Ala Asp
                325                 330                 335

Gly Ser Cys Val Leu Ala Asp Met Ser Asn Arg Leu Thr Ile Phe His
            340                 345                 350

Leu Arg Cys Ser Arg Arg Glu Glu Gln Gln Pro Gly Gln Lys Thr Ser
        355                 360                 365

Val Val Ala Thr Ala Lys Pro Gly Cys Val Ser Ser Gly Thr Asp Ala
    370                 375                 380

Ala Ser Ser Ser His Thr Asn Thr Thr Ser Ala Ala Ala Ser Pro
385                 390                 395                 400

Ala Ser Pro Pro Val Ser Ala Pro Ala Lys Ala Ala Pro Pro Ala
                405                 410                 415
```

```
Ala Ala Arg Ser Ala Glu Pro His Val Gly Ser Lys Ile Ile Ala Asn
            420                 425                 430

Leu Val Asn Gln Leu Gly Ile Asn Val Thr Gln Arg Ser Val Val Ser
        435                 440                 445

Thr Gly Ala Pro Ala Thr Thr Arg Ser Thr Ala Val Thr Ser Thr Thr
        450                 455                 460

Thr Ala Pro Gln Arg Thr Ser Pro Tyr Gly His Asn Gly Arg Pro Val
465                 470                 475                 480

Thr Ala Gly Leu Val Ala Ala Asn Ser Gly Ala Ser Ala Ala Ser Ser
                485                 490                 495

Pro Thr Ala Ala Ala Lys Pro Thr Gly Glu Glu Lys Ala Ser Ala Ala
            500                 505                 510

Cys Glu Thr Ser Ser Val Ala Ile Asn Ala Thr Arg Pro Ala Leu His
            515                 520                 525

Asn Ala Ser Leu Pro Gln Ala Pro Thr Asp Gly Val Leu Ala Ala Ala
        530                 535                 540

Val Tyr Gln Ser Glu Gly Glu Val His Gln Ser Leu Glu Arg Leu Glu
545                 550                 555                 560

Ser Val Ile Thr Asn Thr Ser Arg Val Leu Lys Leu Leu Pro Asp Thr
                565                 570                 575

Ile Arg Arg Asp His Glu Gln Leu Leu Asn Leu Gly Leu Glu Ala Gln
            580                 585                 590

Met Thr Glu Leu Gln Gln Ser Arg Pro Thr Pro Gln Thr Gln Pro Arg
        595                 600                 605

Asp Thr Ser Ser Ala Lys Ser Ser Val Phe Glu Thr Tyr Thr Leu Val
610                 615                 620

Leu Ile Ala Asp Ser Leu Ser Arg Asn Ile Thr Lys Gly Val Lys Arg
625                 630                 635                 640

Gly Val Asn Glu Ala Ile Met Leu His Leu Asp His Glu Val Arg His
                645                 650                 655

Ala Ile Gly Asn Arg Leu Arg Gln Thr Gln Lys Asn Ile Ile Lys Ser
            660                 665                 670

Arg Leu Asp Glu Ala Leu Lys Glu Ser Thr Thr Gln Phe Thr Ala Gln
        675                 680                 685

Leu Thr Gln Thr Val Glu Asn Leu Val Lys Arg Glu Leu Ala Glu Val
        690                 695                 700

Leu Gly Ser Ile Asn Gly Ser Leu Thr Ser Leu Val Lys Glu Asn Ala
705                 710                 715                 720

Ser Leu Lys Lys Glu Leu Asn Ser Ile Met Ser Ser Gly Val Leu Asp
                725                 730                 735

Glu Met Arg Arg Met Arg Glu Glu Leu Cys Thr Leu Arg Glu Ser Val
            740                 745                 750

Ala Lys Arg Lys Ala Thr Met Pro Asp Ser Ser Leu His Ala Thr Ser
            755                 760                 765

Ser Phe Gln Gly Arg Arg Ser Ala Pro Glu Thr Ile Leu Ala Thr Ala
    770                 775                 780

Leu Ser Met Val Arg Glu Gln Gln Tyr Arg Gln Gly Leu Glu Val Met
785                 790                 795                 800

Leu Met Ala Gln Gln Pro Ser Leu Leu Leu Arg Phe Leu Ser Ile Leu
            805                 810                 815

Thr Arg Glu Asn Glu Asn Ala Tyr Ser Glu Leu Ile Glu Asn Val Glu
        820                 825                 830
```

```
Thr Pro Asn Asp Val Trp Cys Ser Val Leu Leu Gln Leu Ile Glu Ala
        835                 840                 845

Ala Ala Thr Glu Ala Glu Lys Glu Val Val Gly Val Ala Ile Asp
    850                 855                 860

Ile Leu Ser Glu Arg Asp Gln Ile Ala Gln Asn Gly Ala Leu Gly Ser
865                 870                 875                 880

Lys Leu Thr Thr Ala Met Arg Ala Phe Glu Arg Gln Ala Arg Ser Glu
                885                 890                 895

Thr Thr Ser Arg Ser Phe Leu Gln Cys Leu Lys Asn Leu Ile Lys Leu
            900                 905                 910

Leu Gln Ser
    915
```

<210> SEQ ID NO 3
<211> LENGTH: 24
<212> TYPE: DNA
<213> ORGANISM: Artificial Sequence
<220> FEATURE:
<223> OTHER INFORMATION: phage DNA primer

<400> SEQUENCE: 3
ggtggcgacg actcctggag cccg                                   24

<210> SEQ ID NO 4
<211> LENGTH: 24
<212> TYPE: DNA
<213> ORGANISM: Artificial Sequence
<220> FEATURE:
<223> OTHER INFORMATION: phage DNA primer

<400> SEQUENCE: 4
ttgacaccag accaactggt aatg                                   24

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
tcgggcactg acgcggcg                                          18

<210> SEQ ID NO 6
<211> LENGTH: 24
<212> TYPE: DNA
<213> ORGANISM: Artificial Sequence
<220> FEATURE:
<223> OTHER INFORMATION: phage lambda gt10 DNA primer

<400> SEQUENCE: 6
cttatgagta tttcttccag ggta                                   24

<210> SEQ ID NO 7
<211> LENGTH: 21
<212> TYPE: DNA
<213> ORGANISM: Artificial Sequence
<220> FEATURE:
<223> OTHER INFORMATION: probe/primer

<400> SEQUENCE: 7
aacgctatta ttagaacagt t                                      21

-continued

```
<210> SEQ ID NO 8
<211> LENGTH: 18
<212> TYPE: DNA
<213> ORGANISM: Artificial Sequence
<220> FEATURE:
<223> OTHER INFORMATION: probe/primer

<400> SEQUENCE: 8
tgcagcagcg gcagaagt                                                 18

<210> SEQ ID NO 9
<211> LENGTH: 22
<212> TYPE: DNA
<213> ORGANISM: Artificial Sequence
<220> FEATURE:
<223> OTHER INFORMATION: probe/primer

<400> SEQUENCE: 9
cagccgacgg tagctgcgtc ct                                            22

<210> SEQ ID NO 10
<211> LENGTH: 21
<212> TYPE: DNA
<213> ORGANISM: Artificial Sequence
<220> FEATURE:
<223> OTHER INFORMATION: probe/primer

<400> SEQUENCE: 10
acataatggc ctcgttcaca c                                             21

<210> SEQ ID NO 11
<211> LENGTH: 34
<212> TYPE: DNA
<213> ORGANISM: Artificial Sequence
<220> FEATURE:
<223> OTHER INFORMATION: probe/primer

<400> SEQUENCE: 11
gactcgctgc agatcgattt tttttttttt tttt                               34

<210> SEQ ID NO 12
<211> LENGTH: 21
<212> TYPE: DNA
<213> ORGANISM: Artificial Sequence
<220> FEATURE:
<223> OTHER INFORMATION: probe/primer

<400> SEQUENCE: 12
cgaagagacc atgaacaact t                                             21

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
gactcgctgc agatcgat                                                 18
```

TRYPANOSOMA CRUZI ANTIGEN, GENE ENCODING THEREFOR AND METHODS OF DETECTING AND TREATING CHAGAS DISEASE

This is a Division of application Ser. No. 08/480,917 filed Jun. 7, 1995 now U.S. Pat. No. 5,820,864. The entire disclosure of the prior application(s) is hereby incorporated by reference herein in its entirety.

FIELD OF THE INVENTION

The subject of the present invention is a new genetic material encoding a new protein recognized by anti-*Trypanosoma cruzi* antisera, and it relates to the use of said gene and protein, especially for diagnostic, pharmaceutical and therapeutic purposes.

BACKGROUND OF THE INVENTION

*Trypanosoma cruzi* is a flagellate protozoal parasite, a member of the order *Kinetoplastida* and of the family Trypanosamatidae, which is responsible for Chagas disease which affects naturally millions of persons, mainly in Latin America.

In vertebrate hosts, *Trypanosoma cruzi* is present in two forms: one which is mobile by means of its flagellum or trypomastigote and which does not divide; the other is aflagellate, or intracellular amastigote, which multiplies by binary division.

Transmission of the protozoan in man occurs through hematophagous insects of the family Reduviidae, during a blood meal followed by dejections at the site of the bite. The vector insect thus releases the infectious metacyclic trypomastigote forms which will colonize many cell types through the blood circulation. *Trypanosoma cruzi* infects cardiac and skeletal muscular cells, the glial cells and the cells of the mononuclear phagocytic system. After passive penetration into the host cell, the trypomastigote form of the parasite differentiates into the amastigote form, divides actively and then this is followed by a release of the trypomastigote forms, thereby causing a new cell invasion.

The insects will complete the parasitic cycle by ingesting, during a blood meal, the trypomastigote forms in the host. The latter differentiate into epimastigote forms in the vector's middle intestine and finally into the infectious metacyclic trypomastigote forms in the posterior intestine, Two phases can be distinguished in the Chagas disease: the acute phase and the chronic phase. The acute phase occurs after a transfusional, congenital or vectorial type contamination and lasts for a few weeks. It is characterized by a large number of parasites circulating in the blood and corresponds to an exponential division of the protozoan. The acute phase is most often asymptomatic. However, in infants contaminated by their mother, the acute phase, which is marked by an acute cardiopathy, may be critical. The chronic phase may extend over many years. In some individuals, this phase is asymptomatic. On the other hand, other patients have tissue lesions in the heart or digestive type manifestations. In any case, clinical diagnosis must always be confirmed by tests for the detection either of antibodies directed against the parasitic antigens, or of the parasite itself.

This disease is becoming a worldwide problem because of the contamination through blood transfusion. It was therefore becoming essential to have available diagnostic tests which make it possible to determine the presence of the parasite in individuals. Various serological tests include direct agglutination, indirect immunofluorescence (IIF), complement fixation tests (CFR), ELISA tests (Enzyme Linked Immunosorbent Assay). The *Trypanosoma cruzi* antigens used for the serological tests are obtained from a total lysate of the noninfectious stage of the parasite or from partially purified protein fractions. However, these fractions do not allow antigens to be obtained in sufficient quantity and quality for the production of a reliable serological diagnostic test. Furthermore, the complexity of the parasite and the strain-to-strain antigenic polymorphism introduce an additional difficulty in the reproducibility of the different preparations. Finally, there are many risks of cross-reactivity with other protozoa, more particularly with *Trypanosoma rangeli*, a nonpathogenic parasite, and the family *Leishmania*. Another disadvantage of these techniques is the absence of determination of the disease phase which would allow a treatment from the onset of the acute phase.

In order to solve these various problems, it was envisaged to produce a serological diagnostic kit composed of recombinant proteins which would be specific for *Trypanosoma cruzi*.

Various research groups have screened libraries for expression of *Trypanosoma cruzi* genomic DNA or complementary DNA in the vector λgt11, using sera from patients suffering from Chagas disease. The λgt11 phage allows the insertion of foreign DNA of a maximum size of 7 Kb into the EcoRI site localized in the lacz gene, under the control of the lac promoter. The product obtained is a recombinant protein used with beta-galactosidase, which is inducible by IPTG (isopropyl beta-D-thiogalactoside).

Various *Trypanosoma cruzi* genes, encoding proteins recognized by the Chagasic sera were thus characterized. Among the recombinant antigens described, the H49 antigen may be mentioned (Paranhos et al., 1994 (1)). However, this antigen does not allow a serological detection sensitivity of 100% of the patients in the acute or chronic phase. It was therefore envisaged to combine the H49 antigen with the CRA antigen (Cytoplasmic Repetitive Antigen) (Lafaille et al., (1989) (2)) but still without solving this problem.

SUMMARY OF THE INVENTION

The present inventors have identified and obtained for the first time a new genetic material encoding a new protein, recognized by anti-*Trypanosoma cruzi* antisera, which makes it possible to overcome the abovementioned disadvantages. The genetic material may be used to produce proteins or polypeptides for the production of diagnostic tests, or for the preparation of vaccinal or pharmaceutical compositions, or may itself either be used as a probe, or for the determination of specific probes which can be used in nucleic acid hybridization tests for the detection of *Trypanosoma cruzi* infections. Likewise, the protein or any corresponding polypeptide may be used for the production of antibodies specific for the parasite, for diagnostic or passive protection purposes.

DETAILED DESCRIPTION OF THE INVENTION

This gene was called Tc 100 by the applicant.

Consequently, the subject of the present invention is a DNA or RNA molecule consisting of at least one strand comprising a nucleotide sequence represented in the identifier SEQ ID NO: 1, or a sequence complementary or antisense or equivalent to said sequence identified in the identifier SEQ ID NO: 1, and especially a sequence having, for any succession of 100 contiguous monomers, at least 50%, preferably at least 60%, or better still at least 85% homology with said sequence.

Nucleotide sequence is understood to mean either a DNA strand or its complementary strand, or an RNA strand or its antisense strand or their corresponding complementary DNAs. The DNA sequence as represented in the identifier SEQ ID NO: 1 corresponds to the messenger RNA sequence, it being understood that the thymine (T) in the DNA is replaced by a uracil (U) in the RNA.

According to the invention, two nucleotide sequences are said to be equivalent in relation to each other, or in relation to a reference sequence if, functionally, the corresponding biopolymers can play essentially the same role, without being identical, with respect to the application or use considered, or in the technique in which they are involved; two sequences obtained because of the natural variability, especially spontaneous mutation, of the species from which they were identified, or because of induced variability, as well as homologous sequences, homology being defined below, are especially equivalent.

Variability is understood to mean any spontaneous or induced modification of a sequence, especially by substitution and/or insertion and/or deletion of nucleotides and/or of nucleotide fragments, and/or extension and/or shortening of the sequence at at least one of the ends; a nonnatural variability may result from the genetic engineering techniques used; this variability may result in modifications of any starting sequence, considered as reference, and capable of being expressed by a degree of homology relative to the said reference sequence.

Homology characterizes the degree of identity of two nucleotide (or peptide) fragments compared; it is measured by the percentage identity which is especially determined by direct comparison of nucleotide (or peptide) sequences, relative to reference nucleotide (or peptide) sequences.

Any nucleotide fragment is said to be equivalent to a reference fragment if it has a nucleotide sequence which is equivalent to the reference sequence; according to the preceding definition, the following are especially equivalent to a reference nucleotide fragment:

a) any fragment capable of at least partially hybridizing with the complementary strand of the reference fragment, b) any fragment whose alignment with the reference fragment leads to the detection of identical contiguous bases, in greater number than with any other fragment obtained from another taxonomic group, c) any fragment resulting or capable of resulting from the natural variability of the species, from which it is obtained, d) any fragment capable of resulting from the genetic engineering techniques applied to the reference fragment, e) any fragment, containing at least 30 contiguous nucleotides, encoding a peptide homologous or identical to the peptide encoded by the reference fragment, f) any fragment different from the reference fragment by insertion, deletion, substitution of at least one monomer, extension or shortening at at least one of its ends. For example any fragment corresponding to the reference fragment flanked at at least one of its ends by a nucleotide sequence not encoding a polypeptide.

The invention moreover relates to DNA or RNA fragments whose nucleotide sequence is identical, complementary, antisense or equivalent to any one of the following sequences:

that starting at nucleotide 1232 and ending at nucleotide 2207 of SEQ ID NO: 1 that starting at nucleotide 1232 and ending at nucleotide 1825 of SEQ ID NO: 1 that starting at nucleotide 1266 and ending at nucleotide 2207 of SEQ ID NO: 1, and especially the DNA or RNA fragments whose sequence has, for any succession of 30 contiguous monomers, at least 50%, preferably at least 60%, or better still at least 85% homology with any one of said sequences.

The subject of the invention is also a protein, called PTc100 by the applicant, having an apparent molecular mass of about 100 kDa, which is recognized by anti-*Trypanosoma cruzi* antisera, or an immunological equivalent of this protein, and fragments thereof. The amino acid sequence of this protein is represented in the identifier sequence SEQ ID NO: 2.

Immunological equivalent is understood to mean any polypeptide or peptide capable of being immunologically recognized by the antibodies directed against said Ptc100 protein.

The invention also relates to any fragment of the Ptc100 protein. A particular protein fragment has a sequence starting at amino acid 323 and ending at amino acid 520 of the sequence defined in the identifier SEQ ID NO: 2, said fragment being specifically recognized by anti-*Trypanosoma cruzi* antisera; the invention also relates to any immunological equivalent of said fragment.

The Ptc100 protein and said protein fragments may contain modifications, especially chemical modifications, which do not alter their immunogenicity.

Moreover, the subject of the present invention is also an expression cassette which is functional especially in a cell derived from a prokaryotic or eukaryotic organism, and which allows the expression of DNA encoding the entire Ptc100 protein or a fragment thereof, in particular of a DNA fragment as defined above, placed under the control of elements necessary for its expression; said protein and said protein fragments being recognized by anti-*Trypanosoma cruzi* antisera.

Generally, any cell derived from a prokaryotic or eukaryotic organism can be used within the framework of the present invention. Such cells are known to persons skilled in the art. By way of examples, there may be mentioned cells derived from a eukaryotic organism, such as the cells derived from a mammal, especially CHO (Chinese Hamster Ovarian) cells; insect cells; cells derived from a fungus, especially a unicellular fungus or from a yeast, especially of the strain *Pichia, Saccharomyces, Schizosaccharomyces* and most particularly selected from the group consisting of *Saccharomyces cerevisiae, Schizosaccharomyces pombe, Schizosaccharomyces malidevorans, Schizosaccharomyces sloofiae, Schizosaccharomyces octosporus*. Likewise, among the cells derived from a prokaryotic organism, there may be used, without this constituting a limitation, the cells of a strain of *Escherichia coli* (*E coli*) or enterobacterial cells. A large number of these cells are commercially available in collections, such as ATCC (Rockville, Mass., USA) and AFRC (Agriculture & Food Research Council, Norfolk, UK). The cell may also be of the wild-type or mutant type. The mutations are described in the literature accessible to persons skilled in the art.

For the purposes of the present invention, an *E. coli* DH5a cell (marketed by the company CLONTECH under the reference: C2007-1) is used.

The expression cassette of the invention is intended for the production of the PTc100 protein or for fragments of said protein which are produced by the abovementioned *E. coli* cell, and which are recognized by human antisera. Such antisera are obtained from patients who have contracted a *Trypanosoma cruzi* infection recently or long ago, and contain immunoglobulins specifically recognizing PTc100. Of course, the PTc100 protein can also be reco ized by other antibodies, such as for example monoclonal or polyclonal antibodies obtained by immunization of various species with the natural abovementioned protein, the recombinant protein or fragments or peptides thereof.

PTc100 protein is understood to mean. the natural *Trypanosoma cruzi* cytoplasmic antigen, or the antigen produced especially by the genetic recombination techniques described in the present application, or any fragment or mutant of this antigen, provided that it is immunologically reactive with antibodies directed against the PTc100 protein of this parasite.

Advantageously, such a protein has an amino acid sequence having a degree of homology of at least 70%, preferably of at least 85%, and most preferably of at least 95% relative to the sequence identified in the identifier SEQ ID NO: 2. In practice, such an equivalent can be obtained by deletion, substitution and/or addition of one or more amino acids of the native or recombinant protein. It is within the capability of persons skilled in the art to perform, using known techniques, these modifications without affecting immunological recognition.

Within the framework of the present invention, the PTc100 protein can be modified in vitro, especially by deletion or addition of chemical groups, such as phosphates, sugars or myristic acids, so as to enhance its stability or the presentation of one or several epitopes.

The expression cassette according to the invention allows the production of a PTc100 protein (having an amino acid sequence as specified above) and fragments of said protein, fused with an exogenous element which can help its stability, its purification, its production or its recognition. The choice of such an exogenous element is within the capability of persons skilled in the art. It may be especially a hapten, an exogenous peptide or a protein.

The expression cassette according to the invention comprises the elements necessary for the expression of said DNA fragment in the cell considered. "Elements necessary for the expression" is understood to mean the elements as a whole which allow the transcription of the DNA fragment into messenger RNA (mRNA) and the translation of the latter into protein.

The present invention also extends to a vector comprising an expression cassette according to the invention. This may be a viral vector and especially a vector derived from a baculovirus, more particularly intended for expression in insect cells, or an adeno-virus-derived vector for expression in mammalian cells.

It may also be an autonomously replicating plasmid vector and in particular a multiplicative vector.

The present invention also relates to a cell derived from a prokaryotic or eukaryotic organism, comprising an expression cassette, either in a form integrated in the cellular genome, or inserted in a vector. Such a cell was previously defined.

The subject of the present invention is also a process for preparing a PTc100 protein, or fragments of said protein, according to which:

(i) a cell derived from a prokaryotic or eukaryotic organism, comprising the expression cassette according to the invention, is cultured under appropriate conditions; and (ii) the expressed protein derived from the abovementioned organism is recovered.

The present invention also relates to one or more peptides, whose amino acid sequence corresponds to a portion of the sequence of the PTc100 protein and exhibiting, alone or as a mixture, a reactivity with the entire sera from individuals or animals infected with *Trypanosoma cruzi*.

The peptides can be obtained by chemical synthesis, lysies of the PTc100 protein or by genetic recombination techniques.

The invention also relates to monoclonal or polyclonal antibodies obtained by immunological reaction of a human or animal organism to an immunogenic agent consisting of the natural or recombinant PTc100 protein and fragments thereof, or of a peptide, as defined above.

The present invention also relates to a reagent for the detection and/or monitoring of a *Trypanosoma cruzi* infection, which comprises, as reactive substance, a PTc100 protein as defined above, or fragments thereof, a peptide or a mixture of peptides as defined above, or at least one monoclonal or polyclonal antibody as described above.

The above reagent may be attached directly or indirectly to an appropriate solid support. The solid support may be especially in the form of a cone, a tube, a well, a bead and the like.

The term "solid support" as used here includes all materials on which a reagent can be immobilized for use in diagnostic tests. Natural or synthetic materials, chemically modified or otherwise, can be used as solid supports, especially polysaccharides such as cellulose-based materials, for example paper, cellulose derivatives such as cellulose acetate and nitro-cellulose; polymers such as vinyl chloride, polyethylene, polystyrenes, polyacrylate or copolymers such as polymers of vinyl chloride and propylene, polymers of vinyl chloride and vinyl acetate; styrene-based copolymers, natural fibers such as cotton and synthetic fibers such as nylon.

Preferably, the solid support is a polystyrene polymer or a butadiene/styrene copolymer. Advantageously, the support is a polystyrene or a styrene-based copolymer comprising between about 10 and 90% by weight of styrene units.

The binding of the reagent onto the solid support may be performed in a direct or indirect manner.

Using the direct manner, two approaches are possible: either by adsorption of the reagent onto the solid support, that is to say by noncovalent bonds (principally of the hydrogen, Van der Walls or ionic type), or by formation of covalent bonds between the reagent and the support. Using the indirect manner, an "anti-reagent" compound capable of interacting with the reagent so as to immobilize the whole onto the solid support can be attached beforehand (by adsorption or covalent bonding) onto the solid support. By way of example, there may be mentioned an anti-PTc100 antibody, on the condition that it is immunologically reactive with a portion of the protein different from that involved in the reaction for recognizing the antibodies in the sera; a ligand-receptor system, for example by grafting onto the PTc100 protein a molecule such as a vitamin, and by immobilizing onto the solid phase the corresponding receptor (for example the biotin-streptavidin system). Indirect manner is also understood to mean the preliminary grafting or fusion by genetic recombination of a protein, or a fragment of this protein, or of a polypeptide, to one end of the PTc100 protein, and the immobilization of the latter onto the solid support by passive adsorption or covalent bonding of the protein or of the polypeptide grafted or fused.

The invention also relates to a process for the detection and/or monitoring of a *Trypanosoma cruzi* infection in a biological sample, such as a blood sample from an individual or an animal likely to have been infected with *Trypanosoma cruzi*, characterized in that said sample and a reagent as defined above are placed in contact, under conditions allowing a possible immunological reaction and the presence of an immune complex with said reagent is then detected.

By way of non-limiting example, there may be mentioned the sandwich-type detection process in one or more stages, as especially described in patents FR 2,481,318 and FR 2,487,983, which consists in reacting a first monoclonal or polyclonal antibody specific for a desired antigen, attached onto a solid support, with the sample, and in revealing the possible presence of an immune complex thus formed using a second anti-body labelled by any appropriate marker known to persons skilled in the art, especially a radioactive isotope, an enzyme, for example peroxidase or alkaline phosphatase and the like, using so-called competition techniques well known to persons skilled in the art.

The subject of the invention is also an active immunotherapeutic composition, especially a vaccinal preparation, which comprises as active ingredient, a natural or recombinant PTc100 protein or fragments thereof, or the peptides identified above, the active ingredient being optionally conjugated with a pharmaceutically acceptable carrier, and optionally an excipient and/or an appropriate adjuvant.

The present invention also covers a pharmaceutical composition intended for the treatment or for the prevention of a *Trypanosoma cruzi* infection in man or in an animal, comprising a therapeutically effective quantity of an expression cassette, a vector, a cell derived from a prokaryotic or eukaryotic organism as defined above, a PTc100 protein according to the invention, or fragments thereof, or an antibody of the invention.

The subject of the present invention is also probes and primers specific for *T. cruzi*, and their uses in diagnostic tests.

The term probe as used in the present invention refers to a DNA or RNA containing at least one strand having a nucleotide sequence which allows hybridization to nucleic acids having a nucleotide sequence as represented in the identifier SEQ ID NO: 1 or a complementary or antisense sequence, or a sequence equivalent to said sequence, and especially a sequence having, for any succession of 5 to 100 contiguous monomers, at least 50%, preferably at least 60%, or even better at least 85% homology with SEQ ID NO: 1 with fragments thereof, or with a synthetic oligonucleotide allowing such a hybridization, nonmodified or comprising one or more modified bases such as inosine, 5-methyldeoxycytidine, deoxyuridine, 5-dimethylaminodeoxyuridine, 2,6-diaminopurine, 5-bromodeoxyuridine or any other modified base. Likewise, these probes may be modified at the level of the sugar, namely the replacement of at least one deoxyribose with a polyamide (P. E. NIELSEN et al. (1991) (13)), or at the level of the phosphate group, for example its replacement with esters, especially chosen from esters of diphosphate, of alkyl and arylphosphonate and of phosphorothioate.

The probes may be much shorter than the sequence identified in the identifier SEQ ID NO: 1. In practice, such probes comprise at least 5 monomers, advantageously from 8 to 50 monomers, having a hybridization specificity, under defined conditions, to form a hybridization complex with DNA or RNA having a nucleotide sequence as defined above.

A probe according to the invention can be used for diagnostic purposes as capture and/or detection probe, or for therapeutic purposes.

The capture probe can be immobilized on a solid support by any appropriate means, that is to say directly or indirectly, for example by covalent bonding or passive adsorption.

The detection probe is labelled by means of a marker chosen from radioactive isotopes, enzymes especially chosen from peroxidase and alkaline phosphatase, and those capable of hydrolyzing a chromogenic, fluorigenic or luminescent substrate, chromophoric chemical compounds, chromogenic, fluorigenic or luminescent compounds, nucleotide base analogs, and biotin.

The probes of the present invention which are used for diagnostic purposes can be used in any known hybridization technique, and especially the so-called "Dot-Blot" technique (Maniatis et al. (1982) (14)), the Southern Blotting technique (Southern E. M. (1975) (15)), the Northern Blotting technique, which is a technique identical to the Southern Blotting technique but which uses RNA as target, and the sandwich technique (Dunn A.R. et al. (1977) (16)). Advantageously, the sandwich technique is used which comprises a specific capture probe and/or a specific detection probe, it being understood that the capture probe and the detection probe must have a nucleotide sequence which is at least partially different.

Another application of the invention is a therapeutic probe for treating infections due to *Trypanosoma cruzi*, said probe being capable of hybridizing in vivo with the DNA or RNA of the parasite to block the translation and/or transcription and/or replication phenomena.

A primer is a probe comprising 5 to 30 monomers, having a hybridization specificity, under predefined conditions, for the initiation of an enzymatic polymerization, for example in an amplification technique such as PCR (Polymerase Chain Reaction), in an elongation process such as sequencing, in a reverse transcription method and the like.

A preferred probe or primer will contain a nucleotide sequence chosen from the sequences SEQ ID NO: 7, SEQ ID NO: 8, SEQ ID NO: 9, SEQ ID NO: 10 and SEQ ID NO: 12.

The invention also relates to a reagent for detecting and/or identifying *Trypanosoma cruzi* in a biological sample, comprising at least one probe as defined above, and in particular a capture probe and a detection probe, either or both corresponding to the above definition.

The invention therefore provides a process for selectively detecting and/or for identifying *Trypanosoma cruzi* in a biological sample, according to which the RNA, extracted from the parasite and optionally denatured, or the DNA, denatured extract, or the DNA obtained from reverse transcription of the RNA, is exposed to at least one probe as defined above and the hybridization of said probe is detected.

The invention will be understood more clearly upon reading the detailed description below which is made with reference to the accompanying figures in which:

EXAMPLE 1

Isolation of the Tc50 Clone

Figure 1:
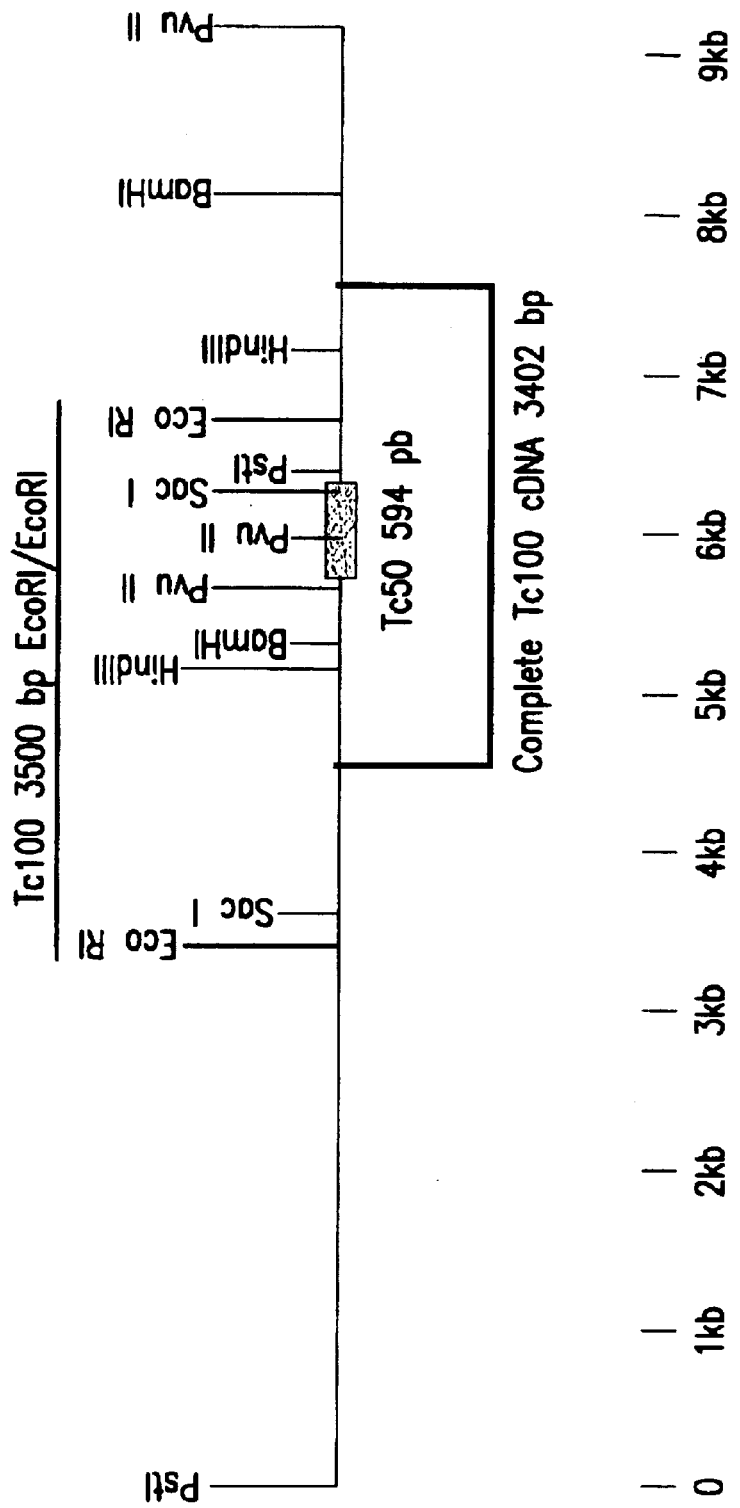
FIG. 1 represents the restriction map of the Tc100 gene, which map is deduced by Southern blotting of different fragments obtained after digestion of *Trypanosoma cruzi* DNA with restriction endonucleases.

An expression library was constructed from *Trypanosoma cruzi* genomic DNA fragments. The *T. cruzi*, strain G (YOSHIDA. N, (1933) (17)), DNA isolated from the metacyclic trypomastigote stage was digested with the enzyme DNase I. After selection of the fragments according to their size, they were ligated to synthetic EcoRI adaptors and cloned into the EcoRI site of lambda gt11 vector DNA (Young and Davis, 1983 (3); Cotrim et al., 1990) (4).

The clone, called Tc50 by the applicant, was isolated from the library by immunological screening with the aid of a mixture of sera from patients suffering from the chronic phase of the Chagas disease.

The Tc50 phage clone was purified, amplified and the insert was detected by the PCR ("Polymerase Chain Reaction") technique with the aid of the primers:

SEQ ID NO: 3 5' (GGTGGCGACGACTCCTGGAGCCCG)3' 24, and

SEQ ID NO: 4 5' (TTGACACCAGACCAACTGGTAATG)3' 24, corresponding respectively to the nucleotide sequence of the left and right arms of the lambda gt11 phage DNA.

The 594 base pairs (bp) Tc50 DNA fragment, after EcoRI digestion, was subcloned into the expression vector pGEX (Pharmacia) linearized with EcoRI. The sequencing of the Tc50 clone DNA was carried out in this same vector with the aid of specific primers situated in 3' and 5' of the cloning site of pGEX, according to the chain termination technique (Sanger et al., 1977 (5)) and according to the manufacturer's procedure (USB-Amersham).

The nucleotide sequence of the 594 bp Tc50 fragment as well as its deduced amino acid sequence (198 aa) are represented in the identifiers SEQ ID NO: 1 and SEQ ID NO: 2 respectively. The nucleotide sequence of the 594 bp Tc50 fragment starts at nucleotide (nt) 1232 and ends at nucleotide 1825 of SEQ ID NO: 1. The corresponding amino acid sequence starts at amino acid 323 and ends at amino acid 520 of SEQ ID NO: 2.

EXAMPLE 2

Expression of the Tc50 Clone in *Escherichia Coli*

The construct pGEX-Tc50 (198 aa) synthesizes, in the bacterium DE5alpha, a protein fused with GST ("Glutathione S Transferase"), with an apparent molecular mass of 50 kDa, which is detected by SDS-PAGE polyacrylamide gel electrophoresis (SDS: sodium dodecyl sulfate) (Laemmli, 1970 (6)). The reactivity of the protein towards chagasic human sera was confirmed by the Western blotting technique (Towbin et al., 1979 (7)) with the aid of the same mixture of chronic phase chagasic sera which is used for screening the lambda gt11 library.

The soluble fraction of the recombinant GST-Tc50 protein obtained after lysis of the bacterial extracts by ultrasound was purified by affinity chromatography on a glutathione agarose column (Sigma), according to the method of Smith and Johnson, (1988) (8).

The antigenic properties of the recombinant GST-Tc50 antigen were tested by ELISA (Voller et al., 1975 (9)). Microtiter plates (Maxisorp (trade name were sensitized with 100 mg/ml of GST-Tc50 antigen in 100 mM NaHCO3 (pH 9.6). After incubation with the patients'sera, the immune complexes were detected with the aid of a peroxidase-coupled anti-human IgG goat serum.

The results are presented in the accompanying table and show that the chagasic human sera tested reacts specifically with the recombinant protein. No cross-reactivity was observed on 7 sera from patients suffering from cutaneous or visceral leishmaniosis.

EXAMPLE 3

Identification of the Native *T. Cruzi* Protein having the Antigenic Determinants of the Tc50 Clone The detection of the native *T. cruzi* protein was performed after immunopurification of a mixture of chagasic human sera on the corresponding recombinant protein called PTc50 by the applicant.

The eluate of monospecific polyclonal anti-bodies which is obtained was used as probe, in Western blotting, on total protein extracts of different stages of the parasite. The selected antibodies specifically reacted with a protein of apparent molecular mass 100 kDa, called PTc100 by the applicant, which is expressed in all the tested strains of the parasite.

EXAMPLE 4

Molecular Analysis of the Tc100 Gene-Southern Blots

In order to establish the restriction map of the Tc100 gene (FIG. 1), the *T. cruzi*, strain G, nuclear DNA was digested with different restriction endonucleases (BamHI, EcoRI, HindIII, PstI, PvuII, SacI, BamHI/EcoRI, BamHI/PvuII, EcoRI/HindIII, EcoRI/PstI, EcoRI/PvuII, EcoRI/SacI, PstI/SacI, PstI/PvuII, PvuII/SacI, PvuII/HindIII), separated on agarose gel and then transferred onto a nylon filter according to the Southern technique. The Southern blot hybridization was performed with the 594 bp Tc50 DNA, which is a fragment of the Tc100 DNA described above, radiolabelled with $^{32}$P by random incorporation (Amersham).

Cloning of a 3500 bp Tc100 Genomic Fragment

According to the results obtained by Southern blotting, the *T. cruzi*, strain G, genomic DNA was digested with the enzyme EcoRI and then separated on agarose gel. The EcoRI restriction fragments of about 3500 bp (FIG. 1) were cloned into the vector lambda gt10 (Huynh et al., 1984 (10)) linearized by EcoRI. The phage clone containing the 3500 bp Tc100 genomic insert was isolated with the aid of the 594 bp radiolabelled probe described above. A 1041 bp fragment situated in the 3' region of the 3500 bp Tc100 genomic insert was sequenced. This sequencing was carried out gradually with the aid of the following primers:

SEQ ID NO: 5 5' (TCGGGCACTGACGCGGCG) 3' 18

SEQ ID NO: 6 5' (CTTATGAGTATTTCTTCCAGGGTA) 3' 24

The primer SEQ ID NO: 5 is situated in the previously sequenced portion of the 594 bp Tc50 fragment. The primer SEQ ID NO: 6 corresponds to the lambda gt10 phage primer.

This 1041 bp fragment, which starts at nucleotide 1403 and ends at nucleotide 2443 of SEQ ID NO: 1, has an open reading frame in phase with the sequence of the 594 bp Tc50 fragment.

EXAMPLE 5

Cloning of the Tc100 cDNA

Figure 2:
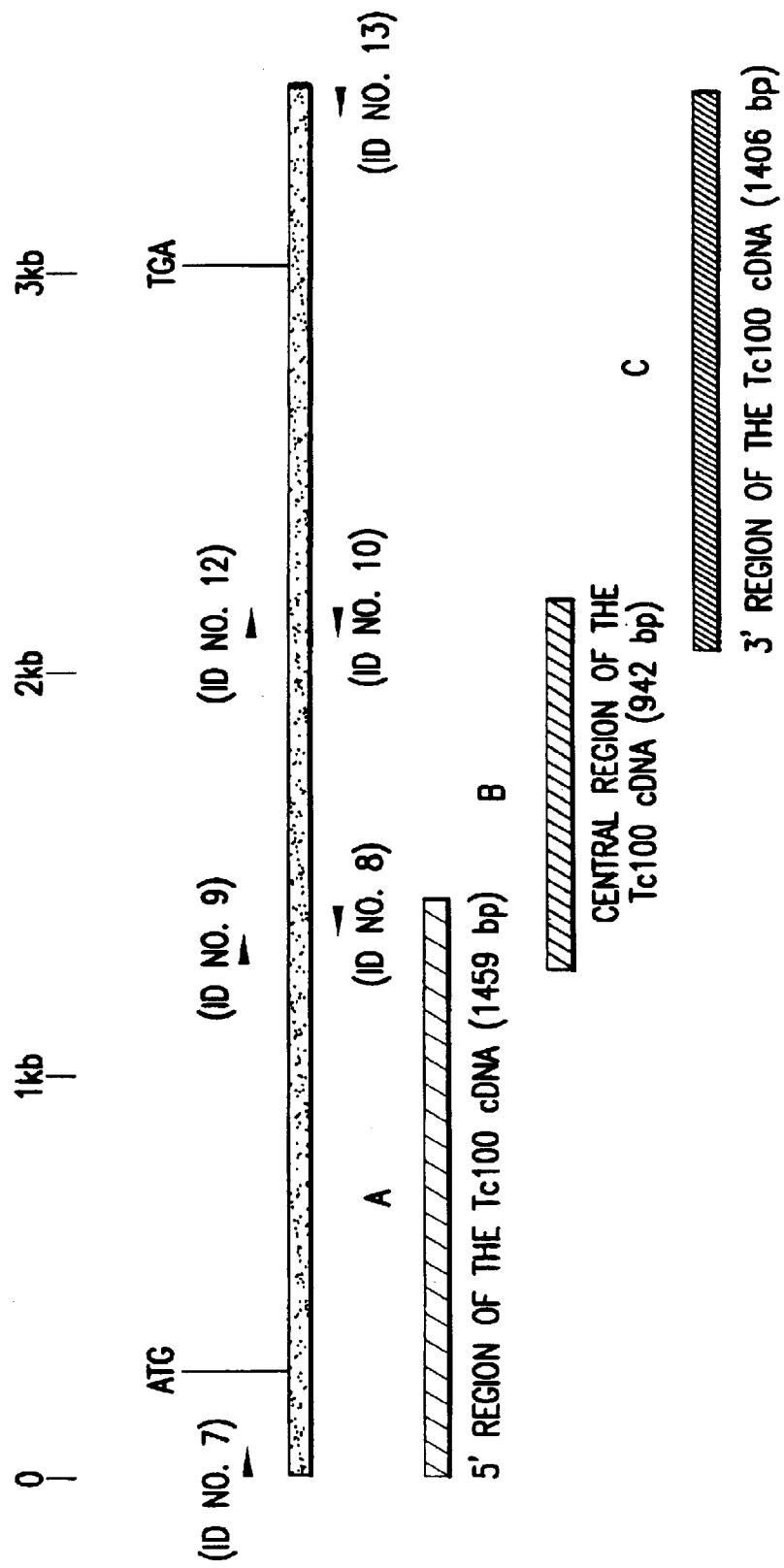
FIG. 2 is a schematic representation of the three overlapping regions of the Tc100 cDNA. The numbered arrows represent the oligonucleotides used as primers for the PCR amplification.

The cDNA was synthesized from total RNA from *T. cruzi*, strain G, epimastigots. The Tc100 CDNA was amplified by the PCR technique in three different fragments: a fragment A corresponding to the 5' region of 1459 bp, a fragment B corresponding to the central region of 942 bp, a fragment C corresponding to the 3' region of 1406 bp of the Tc100 cDNA, as schematically represented in FIG. 2.

Cloning of fragment A of the Tc100 cDNA

The total cDNA synthesized by AMV ("avian myeloblastosis virus") reverse transcriptase, with the aid of random hexanucleotides (Boehringer Mannheim), was amplified, by PCR, using the following pair of primers:

SEQ ID NO: 7 5' (AACGCTATTATTAGAACAGTT)3' 21, and

SEQ ID NO: 8 5' (TGCAGCAGCGGCAGAAGT)3' 18

SEQ ID NO: 7 corresponds to a portion of the consensus sequence of 35 nucleotides present in 5' of the mRNAs in trypanosomatides and called "spliced leader" (Parsons et al. 1984 (11)).

SEQ ID NO: 8 corresponds to the sequence complementary to a portion of the predetermined sequence of the 594 bp fragment, which starts at nucleotide 1442 and ends at nucleotide 1459 of SEQ ID NO: 1 according to the coding strand numbering.

After verification by Southern blotting with the aid of the radiolabelled 594 bp probe previously described, the 1459 bp cDNA fragment corresponding to the 5' region of Tc100 was cloned into the plasmid called pCRII (trade name) (Invitrogen), and sequenced. The sequence represented in the identifier SEQ ID NO: 1 starts at nucleotide 1 and ends at nucleotide 1459.

Cloning of fragment B of the Tc100 CDNA

The T. cruzi total CDNA was amplified by PCR with the aid of the primers:

SEQ ID NO: 9: 5' (CAGCCGACGGTAGCTGCGTCCT)3' 22 and

SEQ ID NO: 10: 5' (ACATAATGGCCTCGTTCACAC)3' 21

The sequence ID NO: 9 which corresponds to a portion of the 594 bp predetermined sequence of the Tc100 gene starts at nucleotide 1266 and ends at nucleotide 1287 of SEQ ID NO: 1.

The sequence SEQ ID NO: 10 corresponds to the sequence complementary to a portion of the 1041 bp previously described sequence of the Tc100 gene. The portion complementary to SEQ ID NO: 10 starts at nucleotide 2187 and ends at nucleotide 2207 of SEQ ID No. 1, according to the coding strand numbering.

The fragment obtained, 942 bp in length, was cloned into the plasmid pCRII and sequenced. The sequence represented in the identifier SEQ ID NO: 1 starts at nucleotide 1266 and ends at nucleotide 2207.

Cloning of fragment C of the Tc100 cDNA

In order to isolate the 3' portion of the Tc100 cDNA, the T. cruzi total cDNA was synthesized with the aid of the adaptor oligo(dT)$_{16}$ hybrid primer. SEQ ID NO: 11 5' (GACTCGCTGCAGATCGATTTTTTTTTTTTTTTT)3' 34 according to the RACE ("Rapid Amplification of cDNA Ends") procedure (Frohman et., 1988 (12)).

The 3' region of the Tc100 cDNA was amplified using the adaptor primer and the following pair of primers:

SEQ ID NO: 12: 5' (CGAAGAGACCATGAACAACTT)3' 21 and

SEQ ID NO: 13: 5' (GACTCGCTGCAGATCGAT)3' 18

The sequence SEQ ID NO: 12 corresponds to a portion of the previously described 1041 bp sequence of the Tc100 gene, starting at nucleotide 1997 and ending at nucleotide 2017.

The sequence SEQ ID NO: 11 corresponds to the arbitrary sequence of the adaptor represented in SEQ ID NO: 11.

After checking by Southern blotting using the 1041 bp radiolabelled fragment previously described, the 3' fragment of the Tc100 cDNA, 1423 bp long, was cloned into pCRII and sequenced. The sequence represented in the identifier SEQ ID NO: 1 starts at nucleotide 1997 and ends at nucleotide 3402.

The Tc100 complete CDNA, 3402 bp in size, was completely sequenced. It has a 2745 bp open reading frame and the deduced amino acid sequence is 915. The methionine codon is in position 266 and the stop codon in position 3011.

The *Trypanosoma cruzi* Tc100 gene encodes the new PTc100 protein of theoretical molecular mass 100 kDa.

Of course, since the DNA sequence of the gene has been fully identified, it is possible to produce the corresponding DNA solely by chemical synthesis, and then to insert the DNA into commercially available DNA vectors, using known techniques from the technology relating to genetic recombination.

TABLE

| Disease | Sera | OD (492 nm) detection threshold = 0.320 |
|---|---|---|
| CHAGAS DISEASE | 1 | 1.358 (+) |
|  | 2 | 1.278 (+) |
|  | 3 | 0.328 (+) |
|  | 4 | 0.404 (+) |
|  | 5 | 1.378 (+) |
|  | 6 | 1.059 (+) |
|  | 7 | 0.895 (+) |
|  | 8 | 1.791 (+) |
|  | 9 | 1.635 (+) |
|  | 10 | 1.427 (+) |
|  | 11 | 1.009 (+) |
|  | 12 | 1.743 (+) |
|  | 13 | 0.530 (+) |
|  | 14 | 1.035 (+) |
|  | 15 | 0.461 (+) |
| CUTANEOUS LEISHMANIOSIS | 16 | 0.291 (−) |
| VISCERAL LEISHMANIOSIS | 17 | 0.071 (−) |
| (Kala azar) | 18 | 0.081 (−) |
|  | 19 | 0.279 (−) |
|  | 20 | 0.098 (−) |
|  | 21 | 0.067 (−) |
|  | 22 | 0.125 (−) |

Bibliographic References

Conventional molecular biology techniques were performed according to the procedures cited in: "Molecular cloning, a laboratory manual". Maniatis T., Fritsch E. F. & Sambrook J. Second edition. Cold Spring Harbor Laboratory Press (New York) (1989).

1. Paranhos-Baccala G., Santos M., Cotrim P., Rassi A., Jolivet M., Camargo M. E. & Da Silveira J F. Detection of antibodies in sera from Chagas disease patients using a *Trypanosoma cruzi* immunodominant recombinant antigen. Parasite Immunology (1994): 16: 165–169.

2. Lafaille J. J., Linss J., Krieger M. A., Padron T. S., De Souza W & Goldenberg S. Structure and expression of two *Trypanosoma cruzi* genes encoding antigenic proteins bearing repetitive epitopes. Molecular tand Biochemical Parasitology. (1989). 35: 127–136.

3. Young R. A. & Davis R. W. Efficient isolation of genes by using antibody probes. Proc. Natl. Acad. Sci. USA. (1983). 80: 1194–1198.

4. Cotrim P. C., Paranhos G., Mortara R. A., Wanderley J., Rassi., Camargo ME. & Da Silveira J. F. Expression in

*Escherichia coli* of a dominant immunogen of *Trypanosoma cruzi* recognized by human chagasic sera. Journal of Clinical Microbiology. (1990). 28(3): 519–524.

5. Sanger F., Nicklen S. & Coulson A. R. DNA sequencing with chain-terminating inhibitors. Proc. Natl. Acad. Sci. USA. (1977). 74: 5463–5467.

6. Laemmli U. K. Cleavage of structural proteins during the assembly of the head of bacteriophage T4. Nature. (1970). 227: 680–685.

7. Towbin H., Staehelin T. & Gordon J. Electrophoretic transfer of proteins from polyacrylamide gels to nitrocellulose sheets: procedure and some applications. Proc. Natl. Acad. Sci. USA. (1979). 76: 4350–4354.

8. Smith D. B. & Johnson K. S. Single step purification of polypeptides expressed in *Escherichia coli* as fusions with glutathione S transferase. Gene. (1988). 67: 31–40.

9. Voller A., Draper C., Bidwell D. E. & Bartlett A. Microplate enzyme-linked immunosorbent assay for Chagas disease. Lancet (1975). 1.: 426–428.

10. Huynh T. V., Young R. A. & Davis R. W. DNA Cloning: A practical approach. (1984) (Ed. D. Glover) 49–78. IRL. Oxford.

11. Parsons M., Nelson R. G., Watkins K. P. & Agabian N. Trypanosome mRNAs share a common 5' Spliced Leader sequence. Cell. (1984). 38: 309–316.

12. Frohman M. A., Dush M. K. & Martin G. R. Rapid production of full lengh [sic] cDNA from rare tran-scripts amplification using a single gene specific oligonucleotide primer. Proc. Natl. Acad. Sci. USA. (1984) 85: 8998–9002.

13. Nielsen P. E. et al., Science, 254, 1497–1500 (1991).

14. Maniatis et al., Molecular Cloning, Cold Spring Harbor (1982).

15. Southern E. M, J. Mol. Biol., 98, 503 (1975).

16. Dunn A. R., Hassel J. A., Cell, 12, 23 (1977).

17. Yoshida N, Surface antigens of metacyclic trypomastigotes of *Trypanosoma cruzi* , Infection and Immunity, 40, 836–839 (1983).

What is claimed is:

1. A synthetic or isolated nucleic acid fragment which comprises a nucleotide sequence that is identical or fully complementary to at least one of: (a) first sequence starting at nucleotide 1232 and ending at nucleotide 1825 of SEQ ID NO: 1 or the corresponding RNA sequence, or (b) a second sequence starting at nuclcotide 1266 and ending at nucleotide 2207 of SEQ ID NO: 1 or the corresponding RNA sequence.

2. The nucleic acid fragment according to claim 1, wherein said nucleotide sequence is identical or fully complementary to a second sequence starting at nucleotide 1232 and ending at nucleotide 2207 of SEQ ID NO: 1 or the corresponding RNA sequence.

3. A probe for identifying *Trypanosoma cruzi*, consisting of:
   (a) a nucleotide sequence selected from the group consisting of: SEQ ID NO: 5, SEQ ID NO: 7, SEQ ID NO: 8, SEQ ID NO: 9 , SEQ ID NO: 10, SEQ ID NO: 12, a nucleotide sequence starting at nucleotide 1232 and ending at nucleotide 1825 of SEQ ID NO: 1, and a nucleotide sequence starting at nucleotide 1403 and ending at nucleolide 2443 of SEQ ID NO: 1,
   (b) a complement of said nucleotide sequence (a), or
   (c) an RNA sequence corresponding to said nucleotide sequence (a) or said complement thereof.

4. A reagent for detecting or identifying *Typanosoma cruzi* in a biological sample, said reagent comprising a capture probe and a detection probe, both in accordance with claim 3, wherein said capture probe and said detection probe have nucleotide sequences that are different from one another.

5. The reagent according to claim 4, wherein said capture probe is attached to a solid support.

6. The reagent according to claim 5, wherein said capture probe is directly attached to said solid support.

7. The reagent according to claim 5, wherein said capture probe is indirectly attached to said solid support.

8. The reagent according to claim 4, wherein said detection probe is labeled by a marker selected from the group consisting of radioactive isotopes, enzymes capable of hydrolyzing a chromogenic, fluorigenic or luminescent substrate, chromophoric chemical compounds, fluorigenic compounds, luminescent compounds, nucleotide base analogs, and biotin.

9. The reagent according to claim 8, wherein said enzymes are selected from the group consisting of peroxidase and alkaline phosphatase.

10. A method for detection and/or identification of *Trypanosoma cruzi* in a biological sample, comprising exposing denatured DNA extracted from *Trypanosoma cruzi* or DNA obtained by reverse transcription of RNA extracted from *Trypanosoma cruzi* to at least one probe according to claim 3; hybridizing said probe with said DNA if present; and detecting hybridization of said probe.

11. A method for detection and/or identification of *Trypanosoma cruzi* in a biological sample, comprising exposing extracted RNA from *Trypanosoma cruzi* to at least one probe according to claim 3; hybridizing said probe with said RNA if present; and detecting said hybridization.

12. A process for detecting and/or identifying *Trypanosoma cruzi* in a biological sample, comprising:
    exposing DNA or RNA from the sample to a probe under such conditions that said probe hybridizes to a nucleotide sequence identical or fully complementary to a sequence starting at nucleotide 1232 and ending at nucleotide 2207 of SEQ ID NO: 1 or the corresponding RNA sequence; and
    detecting hybridization of the probe to said DNA or RNA to detect and/or identify *Trypanosoma cruzi*.

13. A primer for amplifying a *Trypanosoma cruzi* nucleotide sequence, consisting of:
    (a) a nucleotide sequence selected from the group consisting of: SEQ ID NO: 5, SEQ ID NO: 7, SEQ ID NO: 8, SEQ ID NO: 9, SEQ ID NO: 10 and SEQ ID NO: 12,
    (b) a complement of said nucleotide sequence (a), or
    (c) an RNA sequence corresponding to said nucleotide sequence (a) or said complement thereof.

14. The reagent according to claim 4, further comprising at least one primer for amplifying a *Trypanosoma cruzi* nucleotide sequence, consisting of:
    (a) a nucleotide sequence selected from the group consisting of: SEQ ID NO: 5, SEQ ID NO: 7, SEQ ID NO: 8, SEQ ID NO: 9, SEQ ID NO: 10 and SEQ ID NO: 12,
    (b) a complement of said nucleotide sequence (a), or
    (c) an RNA sequence corresponding to said nucleotide sequence (a) or said complement thereof.

15. The method according to claim 10, wherein before said DNA is exposed to said probe, said DNA is amplified in the presence of an enzymatic system with at least one primer for amplifying a *Trypanosoma cruzi* nucleotide sequence, consisting of:
    (a) a nucleotide sequence selected from the group consisting of: SEQ ID NO: 5, SEQ ID NO: 7, SEQ ID NO: 8, SEQ ID NO: 9, SEQ ID NO: 10 and SEQ ID NO: 12,
    (b) a complement of said nucleotide sequence (a), or
    (c) an RNA sequence corresponding to said nucleotide sequence (a) or said complement thereof.

16. A method for detection and/or identification of *Trypanosoma cruzi* in a biological sample, comprising exposing DNA of *Trypanosoma cruzi* to at least one primer according to claim 13, and detecting amplification products.

* * * * *